US012766112B2

(12) United States Patent
Reid

(10) Patent No.: US 12,766,112 B2
(45) Date of Patent: Oct. 20, 2026

(54) COMPOSITIONS INCLUDING TERPENES, CANNABINOID OILS, OR FLAVONOIDS AND USES THEREOF

(71) Applicant: Reidsway, Inc., Porter Ranch, CA (US)

(72) Inventor: Gregory W. Reid, South Pasadena, CA (US)

(73) Assignee: Reidsway, Inc., Porter Ranch (CA)

( * ) Notice: Subject to any disclaimer, the term of this patent is extended or adjusted under 35 U.S.C. 154(b) by 722 days.

(21) Appl. No.: 17/790,405

(22) PCT Filed: Dec. 30, 2020

(86) PCT No.: PCT/US2020/067521

§ 371 (c)(1),
(2) Date: Jun. 30, 2022

(87) PCT Pub. No.: WO2021/138456

PCT Pub. Date: Jul. 8, 2021

(65) Prior Publication Data

US 2023/0165807 A1 Jun. 1, 2023

Related U.S. Application Data

(60) Provisional application No. 62/955,283, filed on Dec. 30, 2019.

(51) Int. Cl.

| | |
|---|---|
| ***A61K 31/045*** | (2006.01) |
| ***A23L 33/00*** | (2016.01) |
| ***A23L 33/105*** | (2016.01) |
| ***A23L 33/115*** | (2016.01) |
| ***A61K 9/127*** | (2025.01) |
| ***A61K 31/01*** | (2006.01) |
| ***A61K 31/015*** | (2006.01) |
| ***A61K 31/05*** | (2006.01) |
| ***A61K 31/121*** | (2006.01) |
| ***A61K 45/06*** | (2006.01) |
| ***A61P 25/20*** | (2006.01) |
| ***A61P 25/28*** | (2006.01) |
| ***C12C 5/02*** | (2006.01) |

(52) U.S. Cl.

CPC .......... *A61K 31/045* (2013.01); *A23L 33/105* (2016.08); *A23L 33/115* (2016.08); *A23L 33/40* (2016.08); *A61K 9/127* (2013.01); *A61K 31/01* (2013.01); *A61K 31/015* (2013.01); *A61K 31/05* (2013.01); *A61K 31/121* (2013.01); *A61K 45/06* (2013.01); *A61P 25/20* (2018.01); *A61P 25/28* (2018.01); *C12C 5/02* (2013.01)

(58) Field of Classification Search

CPC ...... A61K 31/045; A61K 9/127; A61K 31/01; A61K 31/015; A61K 31/05; A61K 31/121; A61K 45/06; A23L 33/105; A23L 33/115; A23L 33/40; A61P 25/20; A61P 25/28; C12C 5/02

See application file for complete search history.

(56) References Cited

U.S. PATENT DOCUMENTS

| | | | | |
|---|---|---|---|---|
| 2014/0298511 | A1 | 10/2014 | Lewis et al. | |
| 2016/0250270 | A1 | 9/2016 | Wendschuh et al. | |
| 2016/0255870 | A1* | 9/2016 | Piorkowski | A23L 2/56 |
| 2019/0076355 | A1* | 3/2019 | Kleidon | A61K 31/192 |
| 2019/0321330 | A1* | 10/2019 | Geiling | A61K 31/352 |

FOREIGN PATENT DOCUMENTS

| | | | | |
|---|---|---|---|---|
| WO | WO-2015042232 | A1 * | 3/2015 | A23L 27/202 |
| WO | 2021/138456 | A1 | 7/2021 | |

OTHER PUBLICATIONS

Google Search; caryophyllene (accessed Mar. 2025) (Year: 2025).*

International Search Report and Written Opinion, mailed Mar. 18, 2021, for International Application Serial No. PCT/US2020/067521 filed on Dec. 30, 2020.

* cited by examiner

*Primary Examiner* — Robert A Wax
*Assistant Examiner* — John W Lippert, III
(74) *Attorney, Agent, or Firm* — K&L Gates LLP; Brian J. Novak; David W. Old

(57) ABSTRACT

Provided herein are compositions including terpenes, cannabinoid oils, or flavonoids, or a combination thereof and uses thereof.

19 Claims, 1 Drawing Sheet

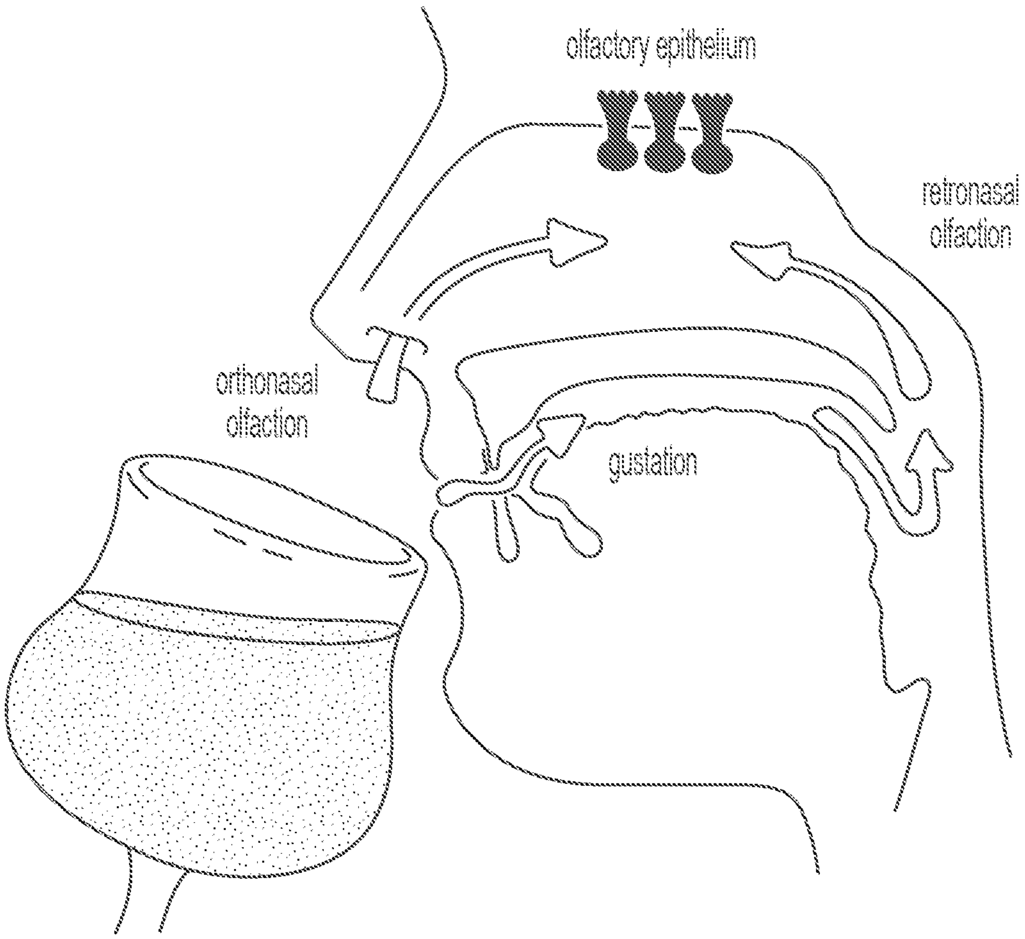
olfactory epithelium
retronasal
olfaction
orthonasal
olfaction
gustation

COMPOSITIONS INCLUDING TERPENES, CANNABINOID OILS, OR FLAVONOIDS AND USES THEREOF

RELATED APPLICATIONS

This application is a national stage entry under 35 U.S.C. § 371 of International application No. PCT/US2020/067521, filed Dec. 30, 2020, which claims priority of U.S. provisional patent application No. 62/955,283, filed Dec. 30, 2019, the entire content of each of which is incorporated by reference herein.

SUMMARY

Described herein are compositions including terpenes, cannabinoid oils, or flavonoids, or a combination thereof, which are ingestible. The compositions can be configured to impart improvements in, for example, cognitive awareness, focus, and alertness while consuming the compositions. In some embodiments, the compositions can be configured to be ingested as a beverage (i.e. as a beverage additive) by an individual. Also provided herein are methods of using and methods of preparing the compositions described herein.

Using an array of terpenes, noticeable and significant improvements in cognitive awareness, focus, and alertness while consuming the compositions, for example, in a variety of beverages, have been discovered. The ability to consume this palatable array of terpenes provide an aromatic and flavor profile that encourages consumption. This leads to cognitive effects that can improve, for example, short term performance, improves motivation, or social engagement. Other effects of consuming the compositions can include clinical outcomes such as elevated mood, elevated focus, brain health, pain relief, anti-inflammation immune health, and respiratory health, for example. Other effects of consuming the compositions can include improved sedation, relaxation, or calming effects. The compositions provided herein present improved compliance, i.e. reduced interaction with, pharmacological interventions, and may be substantially free from drug-drug interactions or metabolic pathway interference. Botanical ingredients can be incorporated into the compositions for therapeutic or experiential effects.

BRIEF DESCRIPTION OF THE DRAWINGS

FIG. 1 shows a schematic of the biology of olfaction and gustation.

DETAILED DESCRIPTION

Terpene blend compositions have been discovered for a variety of beverages, including non-alcoholic or alcoholic beverages. The beverages may be infused (added during beverage bottling) or supplemented (added after bottling prior to imbibing) with the compositions provided herein. In some embodiments, the terpene blend compositions create a new class of drinks that not only taste good, but are beneficial when consumed. Beverages including the compositions provided herein allow for new drinking experiences, including psychosocial and physical sensation experiences.

The psychosocial experience is one of enhanced pleasure with the social aspect, i.e. the enjoyment of the moment with a drink that includes a composition provided herein. The terpene blend compositions provided herein not only add to the flavor and aroma of the first sip, they surprise drinkers with new flavors that continued to improve over the course of a few to several minutes. Most subjects who consumed beverages including a terpene blend composition provided herein said they enjoyed the fresher, brighter flavors and aromas, and they also enjoyed the control that dosing units offered.

There is also a physical experience that comes with consumption of the terpene blend compositions provided herein. Subjects who consumed beverages including a terpene blend composition provided herein reported that they experienced a noticeable feeling of well-being and a sharpened mental brightness. It was also reported that the terpene dosed drinks brightened their outlook and mood and improved social interaction. Many participants in Example 6, below, asked where they could buy the product, indicating satisfaction of a long-felt need for improved characteristics of untreated beverages, including generic beers.

Described herein are compositions including terpenes, which are ingestible. In some embodiments, provided herein are particles including compositions provided herein. The particles may be water soluble, for example, the particles may be particles of a water soluble emulsion. Also provided herein are methods of using and methods of preparing the compositions or particles described herein.

Definitions

As used herein, "apparent attenuation" refers to a measure of the extent of fermentation that wort has undergone in the process of becoming beer. Using gravity units (GU), balling (B), or plato (P) units to express gravity, apparent attenuation is equal to the original gravity minus the final gravity divided by the original gravity. The result is expressed as a percentage.

As used herein, "body" refers to the consistency, thickness, or mouth-filling property of a beer. The sensation of palate fullness in the mouth ranges from thin-bodied to full-bodied.

As used herein, "flocculation" refers to the behavior of suspended particles in wort or beer that tend to clump together in large masses and settle out.

As used herein, "head retention" refers to the foam stability of a beer as measured, in seconds, by time required for a 1-inch foam collar to collapse.

As used herein, "lace" refers to the lacelike pattern of foam sticking to the sides of a glass of a beverage (i.e. beer) once it has been partly or totally emptied.

As used herein, "turbidity" refers to sediment in suspension.

Compositions

Thus, in some embodiments, provided herein are compositions, comprising beta caryophyllene, terpinolene, limonene, and alpha pinene.

In some embodiments, the compositions comprise about 10-25% w/v beta caryophyllene and about 5-15% w/v limonene. In some embodiments, the compositions comprise about 10-25% w/v beta caryophyllene, about 10-20% w/v terpinolene, about 5-15% w/v limonene, and about 5-15% w/v alpha pinene.

In some embodiments, also provided herein are compositions, comprising myrcene, alpha humulene, beta caryophyllene, and linalool.

In some embodiments, provided herein are compositions, comprising about 2-30% w/v myrcene, about 20-30% w/v alpha humulene, about 20-30% w/v beta caryophyllene, and about 5-15% w/v linalool.

In some embodiments, provided herein are compositions, comprising a first mixture including beta caryophyllene, myrcene, limonene, alpha humulene, linalool, and alpha terpineol, and wherein the first mixture optionally includes one or more of beta pinene, alpha pinene, alpha bisabolol, valencene, terpinolene, trans ocimene, or delta 3 carene.

In some embodiments, the compositions further comprise a flavonoid (e.g., xanthohumol).

In some embodiments, the first mixture is present in the composition in a concentration of about 10 to 15 mg/mL. In some embodiments, the first mixture is present in the composition in a concentration of about 13.3 mg/mL. In some embodiments, the first mixture is present in the composition in a concentration of about 20 mg/mL. In some embodiments, the first mixture is present in the composition in a concentration of about 1-50 mg/mL. In some embodiments, the first mixture is present in the composition in a concentration of about 2-40 mg/mL. In some embodiments, beta caryophyllene is present in the first mixture in a concentration of about 20% to about 40% v/v. In some embodiments, beta caryophyllene is present in the first mixture in a concentration of about 15% to about 20% v/v. In some embodiments, myrcene is present in the first mixture in a concentration of about 5% to about 40% v/v. In some embodiments, limonene is present in the first mixture in a concentration of about 2% to about 15% v/v. In some embodiments, alpha humulene is present in the first mixture in a concentration of less than 1% to about 15% v/v. In some embodiments, linalool is present in the first mixture in a concentration of less than 1% to about 5% v/v. In some embodiments, alpha terpineol is present in the first mixture in a concentration of less than 1% to about 5% v/v. In some embodiments, xanthohumol is present in the first mixture. In some embodiments, when present in the first mixture, xanthohumol is present in a concentration of not more than about 20% v/v.

In some embodiments: beta pinene, if present in the first mixture, is present in the first mixture in a concentration of about 2% to about 10% v/v; alpha pinene, if present in the first mixture, is present in the first mixture in a concentration of about 2% to about 10% v/v; alpha bisabolol, if present in the first mixture, is present in the first mixture in a concentration of less than 1% to about 5% v/v; valencene, if present in the first mixture, is present in the first mixture in a concentration of about 5% v/v or less; terpinolene, if present in the first mixture, is present in the first mixture in a concentration of less than 1% to about 20% v/v; trans ocimene, if present in the first mixture, is present in the first mixture in a concentration of less than 1% to about 5% v/v; delta 3 carene, if present in the first mixture, is present in the first mixture in a concentration of less than 1% to about 5% v/v; and xanthohumol, if present in the first mixture, is present in the first mixture in a concentration of less than 1% to about 20%.

In some embodiments, the compositions provided herein further comprise one or more of L-theanine, caffeine, quercetin, green tea extract, vitamin $B_{12}$, or vitamin D. In some embodiments, the compositions provided herein further comprise L-theanine, caffeine, quercetin, green tea extract, vitamin $B_{12}$, and vitamin D.

In some embodiments, the compositions provided herein further comprise one or more of curcumin, cocoa, dark chocolate, galangal, ashwagandha, an adaptogen, or maca root. In some embodiments, the compositions provided herein further comprise curcumin, cocoa, dark chocolate, galangal, ashwagandha, an adaptogen, and maca root.

In some embodiments, the compositions provided herein further comprise one or more of eucalyptol, borneol, phytol, fenchol, nerolidol, geraniol, or farnesol. In some embodiments, the compositions provided herein include alpha bisabolol or terpinolene, or both.

In some embodiments, the botanicals, which may optionally be included in the compositions provided herein, include branched-chain amino acids (BCAAs), guayusa, guarana, bacopa Monnieri, Rhodiola rosea, lion's mane, holy basil (tulsi), schisandra, resveratrol, fish oils, caffeine, phosphatidylserine, acetyl-L-carnitine, L-alpha glycerylphosphorylcholine (alpha GPC), gingko biloba, creatine, green tea, chamomile, a B vitamin, phosphatidylserine, or huperzine A.

In some embodiments, the compositions provided herein include one or more of declinol or an alpha agonist.

In some embodiments, the compositions provided herein include one or more of valerian root, hops extract, melatonin, passion flower, lavender flower, ginseng, glycine, tryptophan, magnolia, black cohosh, dong quai, kava, evening primrose oil, soy, vitamin E, wild yam, or St. Johns Wort.

In some embodiments, the first mixture is encapsulated within a vesicle (i.e. a lipid bilayer vesicle). In some embodiments, the vesicle forms an emulsion in water. In some embodiments, the vesicle is water soluble.

In some embodiments, the compositions provided herein further comprise one or more of vitamin A, vitamin $B_6$, vitamin C, vitamin D, vitamin E, vitamin K, thiamin, riboflavin, niacin, pantothenic acid, pyridoxal, cobalamin, biotin, folate, or folic acid.

In some embodiments, the compositions provided herein further comprise one or more of calcium, phosphorus, potassium, sodium, chloride, magnesium, iron, zinc, iodine, sulfur, cobalt, copper, fluoride, manganese, or selenium.

In some embodiments, the compositions provided herein include vitamin K, potassium, sodium, and magnesium. In some embodiments, the compositions provided herein include potassium, sodium, and magnesium.

In some embodiments, the compositions provided herein further comprise an antioxidant (e.g., vitamin C, vitamin E, selenium, or one or more carotenoids (e.g., beta-carotene, lycopene, lutein, or zeaxanthin), or a combination thereof).

In some embodiments, the compositions provided herein further comprise a flavonoid (e.g., an anthocyanidin, a catechin, a coumarin, a flavan-3-ol, a flavanone, a flavanonol, a flavone, a flavonol, an isoflavone, a xanthone, or a combination thereof).

In some embodiments, the flavonoid is an abyssinone, apigenin, biochanin, daidzein, diosmetin, epicatechin, eriodictyol, fisetin, genistein, hesperidin, kaempferol, luteolin, macluraxanthone, myricetin, naringenin, peonidin, quercetin, rutin, scopoletin, taxifolin, theaflavin, tricin, or a combination thereof.

In some embodiments, the compositions provided herein further include selenium and a flavonoid, selenium and an antioxidant (e.g., vitamin C, vitamin E, or a carotenoid (e.g., beta-carotene, lycopene, lutein, or zeaxanthin)), or selenium, a flavonoid, and an antioxidant.

In some embodiments, the compositions provided herein further include a probiotic or a psychobiotic (e.g., *Lactobacillus helveticus, Bifidobacterium longum, Lactobacillus casei, Lactobacillus plantarum, Lactobacillus acidophilus, Lactobacillus delbrueckii* subsp. *bulgaricus, Bifidobacterium breve, Bifidobacterium infantis, Streptococcus salivarius, Lactobacillus rhamnosus, Lactobacillus gasseri*, or a combination thereof). In some embodiments, the compositions provided herein further include a prebiotic.

In some embodiments, described herein are nutritive ingestible foods or beverages or food or beverage additives, comprising the compositions provided herein. In some embodiments, the beverages referred to herein may be a beer, a wine, water (e.g. a flavored water or a functional water), a tea (e.g., a black tea, a green tea, a chai, or an infusion), a seltzer (e.g., an alcoholic seltzer or a non-alcoholic seltzer), a carbonated beverage, or an energy drink. The tea may include a kombucha. In some embodiments, the beverage may be a nutritive supplement beverage (i.e. a shake, i.e. a protein shake).

In some embodiments, the additives provided herein may be formulated as powders, liquids, gels, or solids. In some embodiments, the additives may be provided as packets suitable for addition to a beverage. In some embodiments, the additive is formulated as a dry powder. In some embodiments, the additive is formulated as a liquid.

In some embodiments, described herein are non-nutritive ingestible foods or beverages or food or beverage additives, comprising the compositions provided herein.

In some embodiments, described herein are emulsions, comprising particles, said particles including the compositions provided herein, the nutritive ingestible foods or beverages or food or beverage additives provided herein, or the non-nutritive foods or beverages or food or beverage additives provided herein encapsulated within a vesicle. In some embodiments, the particles or vesicles refer to droplets. In some embodiments, droplets of the nanoemulsion are about 300 nM in diameter or less. In some embodiments, the droplets of the nanoemulsion are about 10-300 nM in diameter. In some embodiments, the droplets of the nanoemulsion are about 100-200 nM in diameter. In some embodiments, the droplets of the nanoemulsion are about 170 nM in diameter.

In some embodiments, the vesicle is a lipid bilayer vesicle. In some embodiments, the vesicle is an emulsion droplet.

In some embodiments, described herein are emulsions, comprising about 2 wt % cannabinoid (e.g., cannabidiol (CBD), cannabinol (CBN), cannabichromene (CBC), cannabidivarin (CBDV), cannabigerol (CBG), tetrahydrocannabivarin (THCV), CBD acid, CBC acid, CBG acid, CBN acid, THCV acid, or CBDV acid, or a combination thereof) oil or the compositions provided herein, about 2 wt % polysorbate 80, about 1 wt % lecithin, and about 95 wt % water.

In some embodiments, the cannabinoid oil is a cannabigerol (CBG), cannabichromene (CBC), cannabidiol (CBD), tetrahydrocannabinol (THC), cannabinol (CBN), cannabielsoin (CBE), iso-tetrahydrocannabinol (iso-THC), cannabicyclol (CBL), cannabicitran (CBT) oil, an acid thereof, or a combination thereof.

In some embodiments, the cannabinoid oil is a THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), or an acid thereof, or a combination thereof.

In some embodiments, the cannabinoid oil is selected from Table 1, or a combination thereof. In some embodiments, the cannabinoid oil is an isolated and purified cannabinoid oil.

TABLE 1

| Plant cannabinoid oils. |
| --- |
| Cannabigerol-type (CBG) |
| 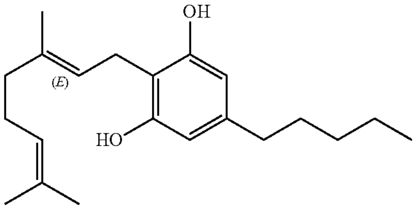 [SMILES: CCCCCc1cc(O)c(C/C=C(\C)CCC=C(C)C)c(O)c1] |
| Cannabigerol<br>(E)-CBG-$C_5$ |
| 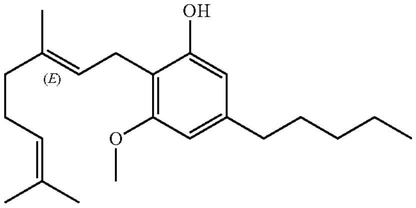 [SMILES: CCCCCc1cc(O)c(C/C=C(\C)CCC=C(C)C)c(OC)c1] |
| Cannabigerol<br>monomethyl ether<br>(E)-CBGM-$C_5$ A |
| 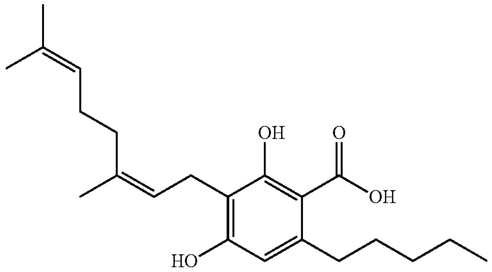 [SMILES: CCCCCc1cc(O)c(C/C=C(/C)CCC=C(C)C)c(O)c1C(=O)O] |
| Cannabinerolic acid<br>A<br>(Z)-CBGA-$C_5$ A |
| 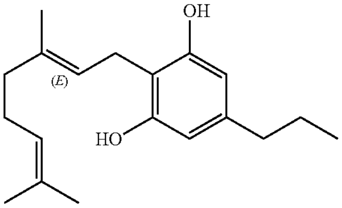 [SMILES: CCCc1cc(O)c(C/C=C(\C)CCC=C(C)C)c(O)c1] |
| Cannabigerovarin<br>(E)-CBGV-$C_3$ |
| 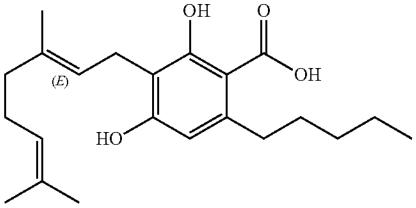 [SMILES: CCCCCc1cc(O)c(C/C=C(\C)CCC=C(C)C)c(O)c1C(=O)O] |

TABLE 1-continued

Plant cannabinoid oils.

Cannabigerolic acid A
(E)-CBGA-$C_5$ A

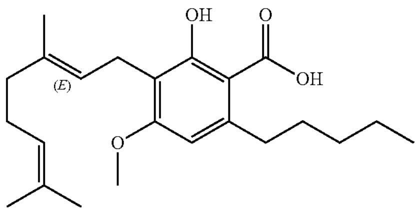 [SMILES: CCCCCc1cc(OC)c(C/C=C(\C)CCC=C(C)C)c(O)c1C(=O)O]

Cannabigerolic acid
A
monomethyl ether
(E)-CBGAM-$C_5$ A

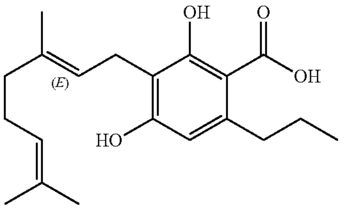 [SMILES: CCCc1cc(O)c(C/C=C(\C)CCC=C(C)C)c(O)c1C(=O)O]

Cannabigerovarinic
acid A
(E)-CBGVA-$C_3$ A

Cannabichromene-type (CBC)

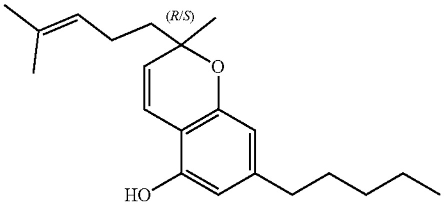 [SMILES: CCCCCc1cc(O)c2c(c1)OC(C)(CCC=C(C)C)C=C2]

(±)-
Cannabichromene
CBC-$C_5$

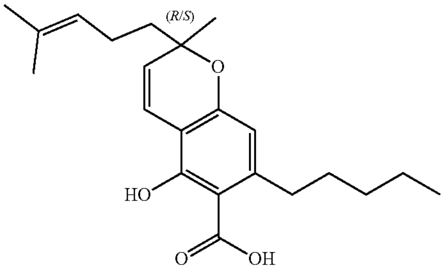 [SMILES: CCCCCc1cc2c(c(O)c1C(=O)O)C=CC(C)(CCC=C(C)C)O2]

(±)-
Cannabichromenic
acid A
CBCA-$C_5$ A

TABLE 1-continued

Plant cannabinoid oils.

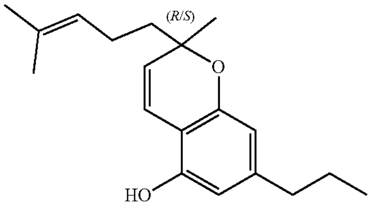 [SMILES: CCCc1cc(O)c2c(c1)OC(C)(CCC=C(C)C)C=C2]

(±)-
Cannabivarichromene,
(±)-
Cannabichromevarin
CBCV-$C_3$

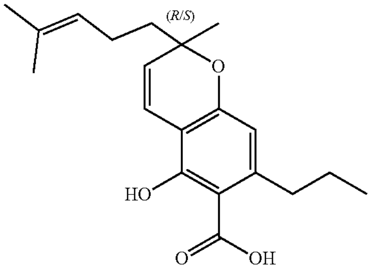 [SMILES: CCCc1cc2c(c(O)c1C(=O)O)C=CC(C)(CCC=C(C)C)O2]

(±)-
Cannabichromevarinic
acid A
CBCVA-$C_3$ A

Cannabidiol-type (CBD)

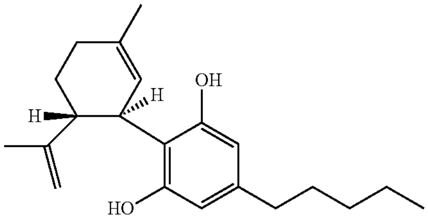 [SMILES: C=C(C)[C@@H]1CCC(C)=C[C@H]1c1c(O)cc(CCCCC)cc1O]

(−)-Cannabidiol
CBD-$C_5$

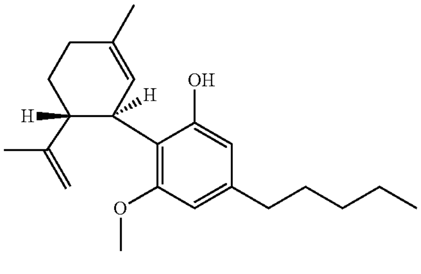 [SMILES: C=C(C)[C@@H]1CCC(C)=C[C@H]1c1c(O)cc(CCCCC)cc1OC]

Cannabidiol
momomethyl ether
CBDM-$C_5$

TABLE 1-continued

Plant cannabinoid oils.

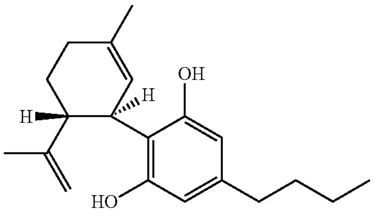 [SMILES: C=C(C)[C@@H]1CCC(C)=C[C@H]1c1c(O)cc(CCCC)cc1O]

Cannabidiol-$C_4$
CBD-$C_4$

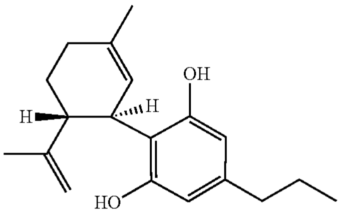 [SMILES: C=C(C)[C@@H]1CCC(C)=C[C@H]1c1c(O)cc(CCC)cc1O]

(−)-Cannabidivarin
CBDV-$C_3$

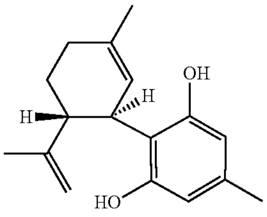 [SMILES: C=C(C)[C@@H]1CCC(C)=C[C@H]1c1c(O)cc(C)cc1O]

Cannabidiorcol
CBD-$C_1$

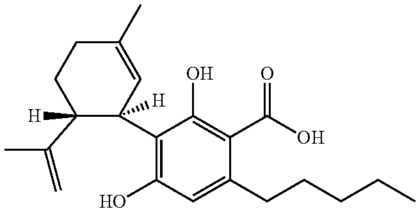 [SMILES: C=C(C)[C@@H]1CCC(C)=C[C@H]1c1c(O)cc(CCCCC)c(C(=O)O)c1O]

Cannabidiolic acid
CBDA-$C_5$

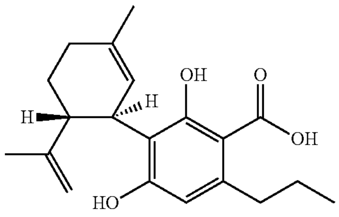 [SMILES: C=C(C)[C@@H]1CCC(C)=C[C@H]1c1c(O)cc(CCC)c(C(=O)O)c1O]

Cannabidivarinic acid
CBDVA-$C_3$

TABLE 1-continued

Plant cannabinoid oils.

Cannabinodiol-type (CBND)

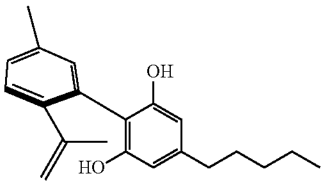

Cannabinodiol
CBND-$C_5$

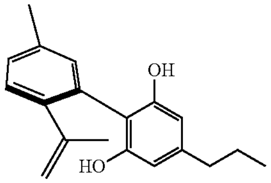

Cannabinodivarin
CBND-$C_3$

Tetrahydrocannabinol-type (THC)

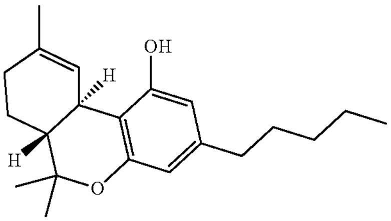 [SMILES: CCCCCc1cc(O)c2c(c1)OC(C)(C)[C@@H]1CCC(C)=C[C@@H]21]

$\Delta^9$-Tetrahydrocannabinol
$\Delta^9$-THC-$C_5$

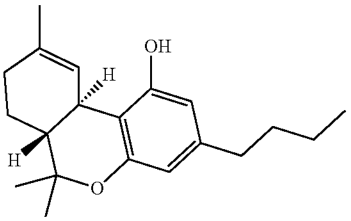 [SMILES: CCCCc1cc(O)c2c(c1)OC(C)(C)[C@@H]1CCC(C)=C[C@@H]21]

$\Delta^9$-Tetrahydrocannabinol-$C_4$
$\Delta^9$-THC-$C_4$

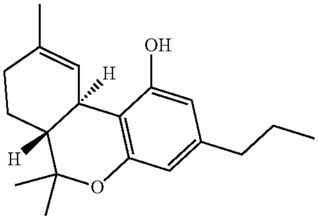 [SMILES: CCCc1cc(O)c2c(c1)OC(C)(C)[C@@H]1CCC(C)=C[C@@H]21]

$\Delta^9$-Tetrahydrocannabivarin
$\Delta^9$-THCV-$C_3$

TABLE 1-continued

Plant cannabinoid oils.

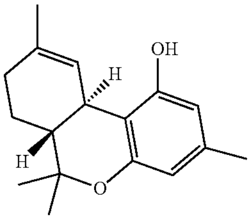 [SMILES: CC1=C[C@H]2c3c(O)cc(C)cc3OC(C)(C)[C@@H]2CC1]

$\Delta^9$-Tetrahydrocannabiorcol
$\Delta^9$-THCO-$C_1$

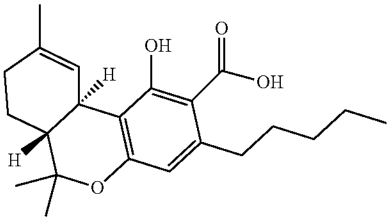 [SMILES: CCCCCc1cc2c(c(O)c1C(=O)O)[C@@H]1C=C(C)CC[C@H]1C(C)(C)O2]

$\Delta^9$-Tetrahydro-cannabinolic acid A
$\Delta^9$-THCA-$C_5$ A

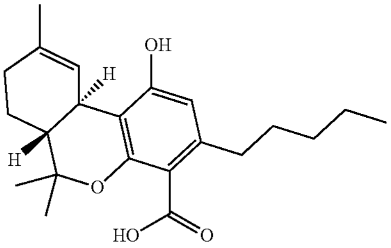 [SMILES: CCCCCc1cc(O)c2c(c1C(=O)O)OC(C)(C)[C@@H]1CCC(C)=C[C@@H]21]

$\Delta^9$-Tetrahydro-cannabinolic acid B
$\Delta^9$-THCA-$C_5$ B

A and/or B

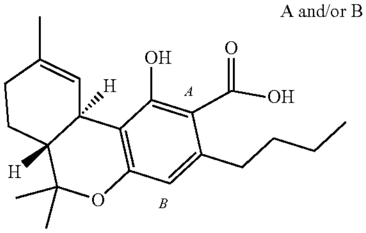

$\Delta^9$-Tetrahydro-cannabinolic acid-$C_4$
A and/or B
$\Delta^9$-THCA-$C_4$ A
and/or B

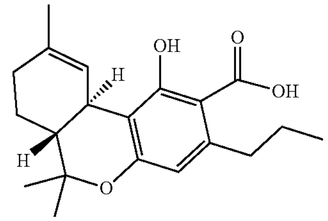 [SMILES: CCCc1cc2c(c(O)c1C(=O)O)[C@@H]1C=C(C)CC[C@H]1C(C)(C)O2]

TABLE 1-continued

Plant cannabinoid oils.

$\Delta^9$-Tetrahydro-cannabivarinic acid A
$\Delta^9$-THCVA-$C_3$ A

A and/or B

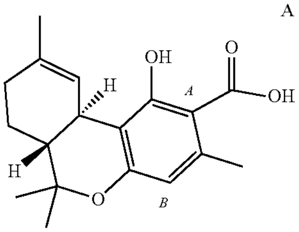

$\Delta^9$-Tetrahydro-cannabiorcolic acid
A and/or B
$\Delta^9$-THCOA-$C_1$ A
and/or B

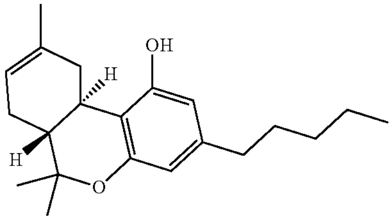 [SMILES: CCCCCc1cc(O)c2c(c1)OC(C)(C)[C@@H]1CC=C(C)C[C@@H]21]

(−)-$\Delta^8$-trans-(6aR,10aR)-$\Delta^8$-Tetrahydrocannabinol
$\Delta^8$-THC-$C_5$

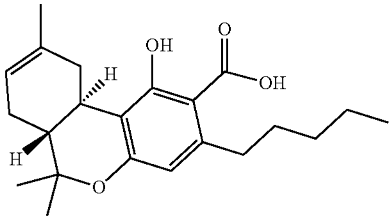 [SMILES: CCCCCc1cc2c(c(O)c1C(=O)O)[C@@H]1CC(C)=CC[C@H]1C(C)(C)O2]

(−)-$\Delta^8$-trans-(6aR,10aR)-Tetrahydrocannabinolic acid A
$\Delta^8$-THCA-$C_5$ A

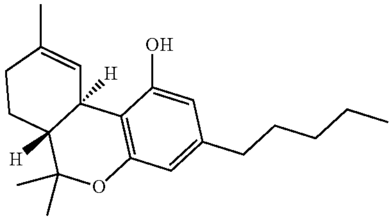 [SMILES: CCCCCc1cc(O)c2c(c1)OC(C)(C)[C@@H]1CCC(C)=C[C@@H]21]

(−)-(6aS,10aR)-$\Delta^9$-Tetrahydrocannabinol
(−)-cis-$\Delta^9$-THC-$C_5$

TABLE 1-continued

Plant cannabinoid oils.

Cannabinol-type (CBN)

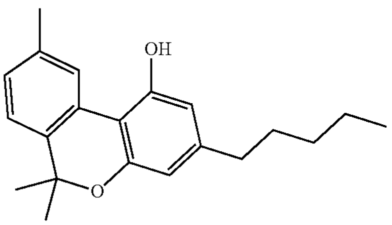 [SMILES: CCCCCc1cc(O)c2c(c1)OC(C)(C)c1ccc(C)cc1-2]

Cannabinol
CBN-$C_5$

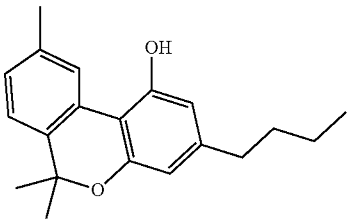 [SMILES: CCCCc1cc(O)c2c(c1)OC(C)(C)c1ccc(C)cc1-2]

Cannabinol-$C_4$
CBN-$C_4$

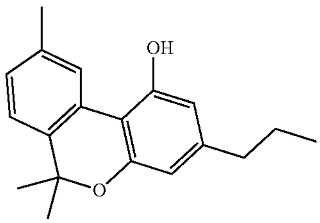 [SMILES: CCCc1cc(O)c2c(c1)OC(C)(C)c1ccc(C)cc1-2]

Cannabivarin
CBN-$C_3$

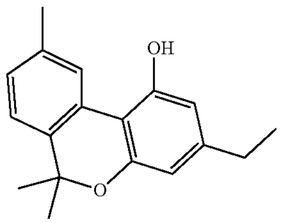 [SMILES: CCc1cc(O)c2c(c1)OC(C)(C)c1ccc(C)cc1-2]

Cannabinol-$C_2$
CBN-$C_2$

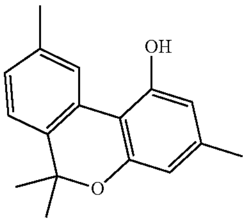 [SMILES: Cc1cc(O)c2c(c1)OC(C)(C)c1ccc(C)cc1-2]

Cannabiorcol
CBN-$C_1$

TABLE 1-continued

Plant cannabinoid oils.

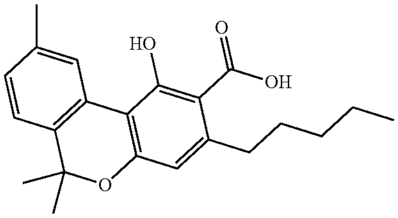 [SMILES: CCCCCc1cc2c(c(O)c1C(=O)O)-c1cc(C)ccc1C(C)(C)O2]

Cannabinolic acid A
CBNA-$C_6$ A

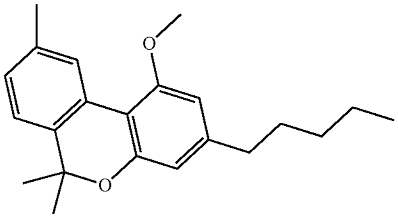 [SMILES: CCCCCc1cc(OC)c2c(c1)OC(C)(C)c1ccc(C)cc1-2]

Cannabinol methyl ether
CBNM-$C_5$

Cannabitriol-type (CBT)

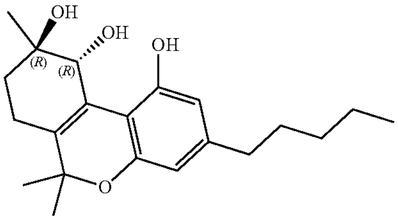

(−)-(9R,10R)-trans-Cannabitriol
(−)-trans-CBT-$C_5$

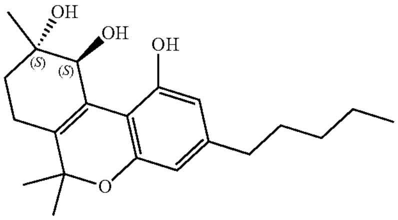

(+)-(9S,10S)-Cannabitriol
(+)-trans-CBT-$C_5$

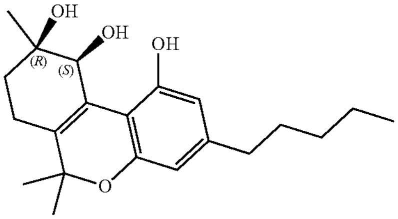

(±)-(9R,10S/9S,10R)-Cannabitriol
(±)-cis-CBT-$C_5$

TABLE 1-continued

| Plant cannabinoid oils. |
|---|
| 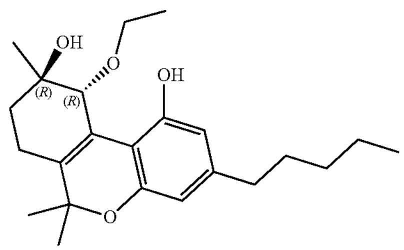 |
| (−)-(9R,10R)-trans-<br>10-O-Ethyl-<br>cannabitriol<br>(−)-trans-CBT-<br>OEt-$C_5$ |
| 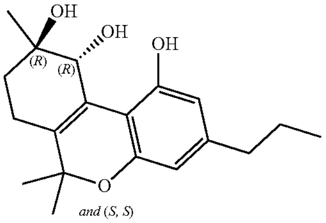<br>and (S, S) |
| (±)-<br>(9R,10R/9S,10S)-<br>Cannabitriol-$C_3$<br>(±)-trans-CBT-$C_3$ |
| 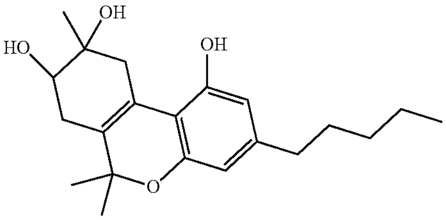 [SMILES: CCCCCc1cc(O)c2c(c1)OC(C)(C)C1=C2CC(C)(O)C(O)C1] |
| 8,9-Dihydroxy-$\Delta^{6a(10a)}$-<br>tetrahydrocannabinol<br>8,9-Di-OH-CBT-$C_5$ |
| 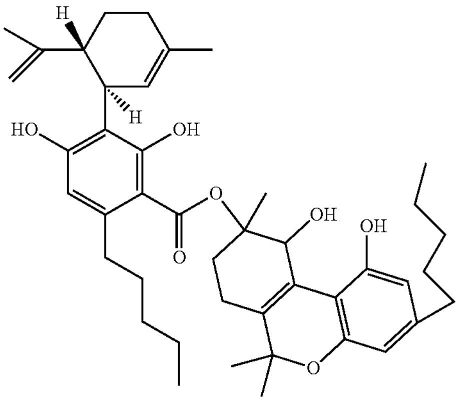 [SMILES: C=C(C)[C@@H]1CCC(C)=C[C@H]1c1c(O)cc(CCCCC)c(C(=O)OC2(C)CCC3=C(c4c(O)cc(CCCCC)cc4OC3(C)C)C2O)c1O] |
| Cannabidiolic acid<br>A<br>cannabitriol ester<br>$CBDA-C_5$ 9-OH-<br>$CBT-C_5$ ester |

TABLE 1-continued

| Plant cannabinoid oils. |
|---|
| 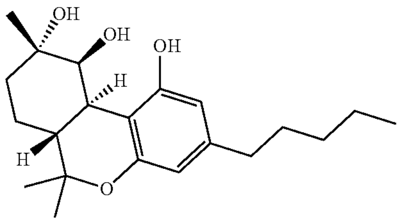 [SMILES: CCCCCc1cc(O)c2c(c1)OC(C)(C)[C@@H]1CC[C@](C)(O)[C@@H](O)[C@@H]21] |
| (−)-<br>(6aR,9S,10S,10aR)-<br>9,10-Dihydroxy-<br>hexahydrocannabinol,<br>Cannabiripsol<br>Cannabiripsol-$C_5$ |
| 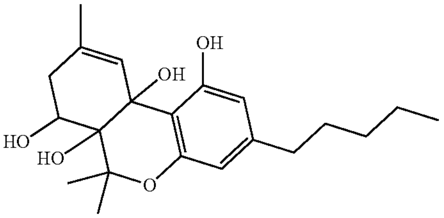 [SMILES: CCCCCc1cc(O)c2c(c1)OC(C)(C)C1(O)C(O)CC(C)=CC21O] |
| (−)-6a,7,10a-<br>Trihydroxy-<br>$\Delta^9$-<br>tetrahydrocannabinol<br>(−)-Cannabitetrol |
| 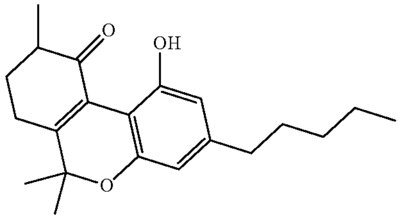 [SMILES: CCCCCc1cc(O)c2c(c1)OC(C)(C)C1=C2C(=O)C(C)CC1] |
| 10-Oxo-$\Delta^{6a(10a)}$-<br>tetrahydrocannabinol<br>OTHC |
| Cannabielsoin-type (CBE) |
| 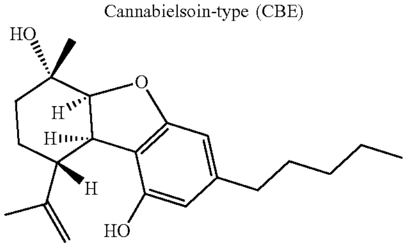 |
| (5aS,6S,9R,9aR)-<br>Cannabielsoin<br>$CBE-C_5$ |
| 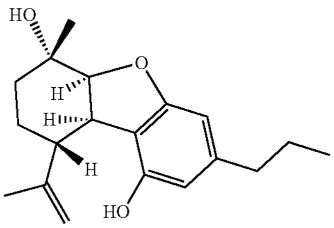 |

TABLE 1-continued

| Plant cannabinoid oils. |
|---|
| (5aS,6S,9R,9aR)-<br>$C_3$-Cannabielsoin<br>CBE-$C_3$ |
| 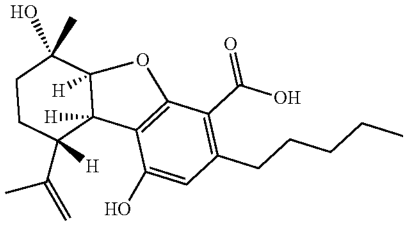 |
| (5aS,6S,9R,9aR)-<br>Cannabielsoic acid A<br>CBEA-$C_5$ A |
| 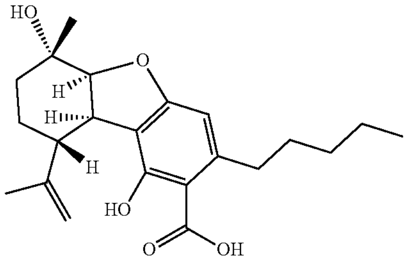 |
| (5aS,6S,9R,9aR)-<br>Cannabielsoic acid B<br>CBEA-$C_5$ B |
| 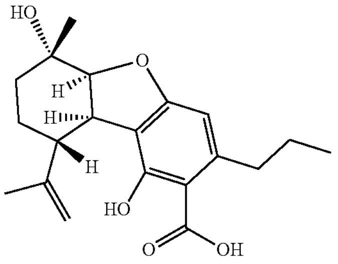 |
| (5aS,6S,9R,9aR)-<br>$C_3$-Cannabielsoic<br>acid B<br>CBEA-$C_3$ B |
| 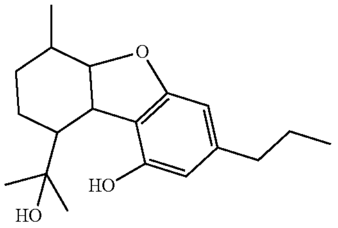 [SMILES: CCCc1cc(O)c2c(c1)OC1C(C)CCC(C(C)(C)O)C21] |
| Cannabiglendol-$C_3$<br>OH-iso-HHCV-$C_3$ |

TABLE 1-continued

| Plant cannabinoid oils. |
|---|
| 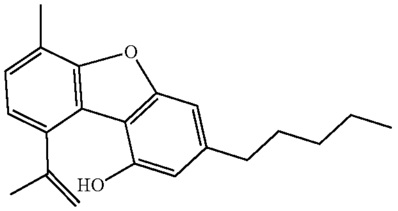 [SMILES: C=C(C)c1ccc(C)c2oc3cc(CCCCC)cc(O)c3c12] |
| Dehydrocannabifuran<br>DCBF-$C_5$ |
| 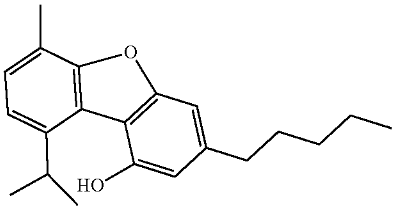 [SMILES: CCCCCc1cc(O)c2c(c1)oc1c(C)ccc(C(C)C)c12] |
| Cannabifuran<br>DCBF-$C_5$ |
| Isocannabinoids |
| 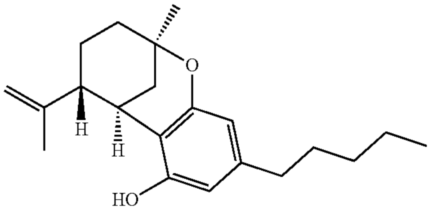 [SMILES: C=C(C)[C@@H]1CC[C@]2(C)C[C@H]1c1c(O)cc(CCCCC)cc1O2] |
| (−)-$\Delta^7$-trans-<br>(1R,3R,6R)-<br>Isotetrahydrocannabinol |
| 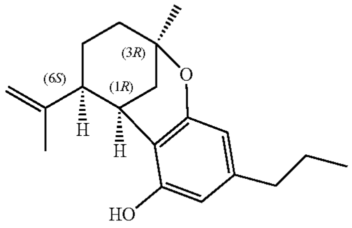<br>and (1S, 3S, 6R) |
| (±)-$\Delta^7$-1,2-cis-<br>(1R,3R,6S/1S,3S,6R)-<br>Isotetrahydro-<br>cannabivarin |
| 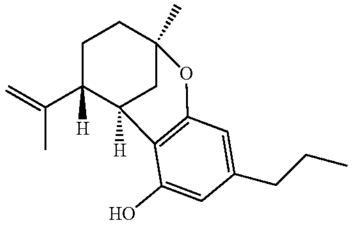 [SMILES: C=C(C)[C@@H]1CC[C@]2(C)C[C@H]1c1c(O)cc(CCC)cc1O2] |
| (−)-$\Delta^7$-trans-<br>(1R,3R,6R)-<br>Isotetrahydrocannabivarin |

TABLE 1-continued

| Plant cannabinoid oils. |
|---|

Cannabicyclol-type (CBL)

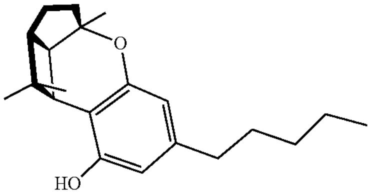

(±)-
(1aS,3aR,8bR,8cR)-
Cannabicyclol
CBL-$C_5$

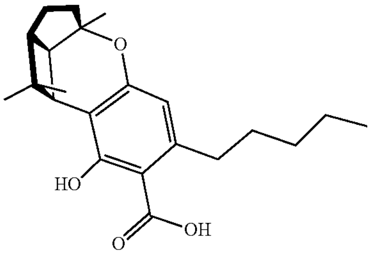

(±)-
(1aS,3aR,8bR,8cR)-
Cannabicyclolic
acid A
CBLA-$C_5$ A

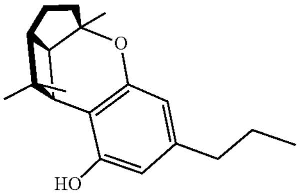

(±)-
(1aS,3aR,8bR,8cR)-
Cannabicyclovarin
CBLV-$C_3$

Cannabicitran-type (CBT)

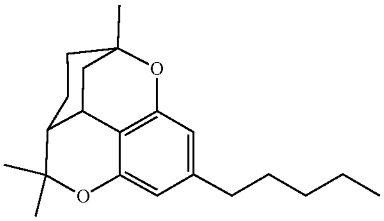
;

Cannabicitran
CBT-$C_5$

Cannabichromanone-type (CBCN)

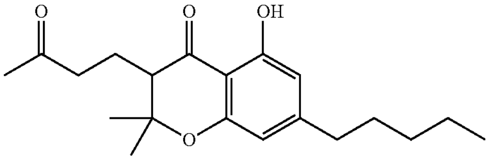 [SMILES: CCCCCc1cc(O)c2c(c1)OC(C)(C)C(CCC(C)=O)C2=O]

TABLE 1-continued

| Plant cannabinoid oils. |
|---|

Cannabichromanone
CBCN-$C_5$

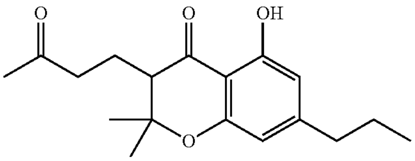 [SMILES: CCCc1cc(O)c2c(c1)OC(C)(C)C(CCC(C)=O)C2=O]

Cannabichromanone-$C_3$
CBCN-$C_3$

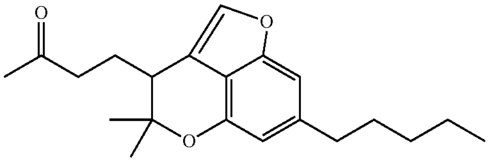 [SMILES: CCCCCc1cc2c3c(coc3c1)C(CCC(C)=O)C(C)(C)O2]

Cannabicoumaronone
CBCON-$C_5$

In some embodiments, described herein are emulsions, comprising about 5 wt % CBD oil or the composition provided herein, about 3.3 wt % polysorbate 80, about 1.7 wt % lecithin, and about 90 wt % water.

In some embodiments provided herein are kits, comprising the compositions provided herein, the nutritive ingestible foods or beverages or food or beverage additives provided herein, or the non-nutritive foods or beverages or food or beverage additives provided herein encapsulated within a vesicle, and instructions for use thereof.

Methods

Also provided herein are methods of use for the compositions provided herein.

Thus, in some embodiments, provided herein are methods of modulating acuity in a subject, comprising administering to the subject an effective amount of an ingestible component.

In some embodiments, provided herein are methods of modulating cognitive awareness in a subject, comprising administering to the subject an effective amount of an ingestible component.

In some embodiments, provided herein are methods of modulating focus in a subject, comprising administering to the subject an effective amount of an ingestible component.

In some embodiments, provided herein are methods of modulating alertness in a subject, comprising administering to the subject an effective amount of an ingestible component.

In some embodiments, provided herein are methods of modulating short term performance in a subject, comprising administering to the subject an effective amount of an ingestible component.

In some embodiments, provided herein are methods of modulating motivation in a subject, comprising administering to the subject an effective amount of an ingestible component.

In some embodiments, provided herein are methods of modulating social engagement in a subject, comprising administering to the subject an effective amount of an ingestible component.

In some embodiments, provided herein are methods of modulating mood in a subject, comprising administering to the subject an effective amount of an ingestible component.

In some embodiments, provided herein are methods of modulating brain health in a subject, comprising administering to the subject an effective amount of an ingestible component.

In some embodiments, provided herein are methods of modulating pain relief in a subject, comprising administering to the subject an effective amount of an ingestible component.

In some embodiments, provided herein are methods of modulating anti-inflammation in a subject, comprising administering to the subject an effective amount of an ingestible component.

In some embodiments, provided herein are methods of modulating respiratory health in a subject, comprising administering to the subject an effective amount of an ingestible component.

In some embodiments, provided herein are methods of modulating sedation in a subject, comprising administering to the subject an effective amount of an ingestible component.

In some embodiments, provided herein are methods of modulating gustation of an ingestible food or beverage in a subject, comprising administering to the subject the ingestible food or beverage and an effective amount of an ingestible component.

In some embodiments, provided herein are methods of modulating olfaction (i.e. orthonasal olfaction, retronasal olfaction, or both) of an ingestible food or beverage in a subject, comprising administering to the subject the ingestible food or beverage and an effective amount of an ingestible component.

In some embodiments, provided herein are methods of modulating anxiety in a subject, comprising administering to the subject an effective amount of an ingestible component.

In some embodiments, modulating anxiety is reducing one or more anxiety hormone levels in the subject.

In some embodiments, provided herein are methods of reducing hormone release signals in a subject, comprising administering to the subject an effective amount of an ingestible component. In some embodiments the hormone release signal is a signal from salivary immunoglobulin A.

In some embodiments, provided herein are methods of modulating stress in a subject, comprising administering to the subject an effective amount of an ingestible component.

In some embodiments, modulating stress is reducing one or more stress hormone levels in the subject.

In some embodiments, the modulating is enhancing.

In some embodiments, provided herein are methods of increasing gamma-aminobutyric acid production in a subject in need thereof, comprising administering to the subject an effective amount of an ingestible component.

In some embodiments, provided herein are methods of modulating calm in a subject, comprising administering to the subject an effective amount of an ingestible component.

In some embodiments, provided herein are methods of modulating relaxation in a subject, comprising administering to the subject an effective amount of an ingestible component.

In some embodiments, provided herein are methods of increasing 5-hydroxytryptamine production in a subject in need thereof, comprising administering to the subject an effective amount of an ingestible component.

In some embodiments of the methods provided herein, the ingestible component includes one or more of the compositions provided herein, an effective amount of one or more of the nutritive ingestible foods or beverages or food or beverage additives provided herein, an effective amount of one or more of the non-nutritive foods or beverages or food or beverage additives provided herein, an effective amount of one or more of the particles provided herein, or an effective amount of one or more of the emulsions provided herein, or a combination thereof.

In some embodiments, provided herein are methods of preparing an ingestible beverage, wherein the ingestible beverage includes a beverage and an ingestible component, comprising combining the beverage and the ingestible component to form the ingestible beverage, wherein the ingestible component includes one or more of the compositions provided herein, an amount of one or more of the nutritive ingestible foods or beverages or food or beverage additives provided herein, an amount of one or more of the non-nutritive foods or beverages or food or beverage additives provided herein, an amount of one or more of the particles provided herein, or an amount of one or more of the emulsions provided herein, or a combination thereof.

In some embodiments, provided herein are methods of modulating the organoleptic hop profile of a beverage comprising adding a composition provided herein to the beverage. In some embodiments, the modulation is causing the organoleptic hop profile to become more apparent. In some embodiments, the modulation is causing the organoleptic hop profile to become less apparent.

In some embodiments, the ingestible component preserves, or improves, mouthfeel of the ingestible food or beverage in the subject.

In some embodiments, the ingestible beverage includes a mouthfeel that is about the same as, or improved with respect to, that of the beverage.

In some embodiments, the mouthfeel includes texture, pH, carbonation, serving temperature, alcohol by volume, fullness, aftertaste, or a combination thereof.

In some embodiments, the ingestible beverage includes an apparent structure that is about the same as, or improved with respect to, that of the beverage.

In some embodiments, the apparent structure includes the apparent bifurcated structure, the apparent beverage foam collar, the apparent beverage body, or a combination thereof.

In some embodiments, the ingestible beverage includes an apparent attenuation that is not more than about 5% (e.g., not more than about 4%, 3%, 2%, or 1%, or less than 1%, or less than 0.5%) different than that of the beverage.

In some embodiments, the apparent attenuation of the beverage or the ingestible beverage is about 65% to about 80% (e.g., about 65%, 70%, 75%, or 80%).

In some embodiments, the beverage optionally includes flocculation (i.e. flocculation is included, or there is no observable flocculation, i.e. there is no flocculation).

In some embodiments, the beverage is an alcoholic beverage (e.g., a fermented alcoholic beverage, e.g., ale, lager, champagne, or wine). In some embodiments, the beverage is a beer.

In some embodiments, the beverage is:

an ale, a cask ale, a kellerbier, a lager, a strong ale, a sour ale, a wheat beer, or a zwickelbier; or a fruit beer, an herbed beer, a spiced beer, a honey beer, a rye beer, a smoked beer, a vegetable beer, a wild beer, or a wood-aged beer; or a bouza, a boza, a bozo, a braggot, a cauim, a chhaang, a chichi, a gotlandsdricka, a grisette, a gruit, a kvass, an oshikundu, a purl, a sahti, a sato, a lao hai, or a sulima; or an altbier, an amber ale, a barley wine, a berliner weisse, a biére de garde, a bitter, a blonde ale, a bock, a brown ale, a steam beer, cream ale, a dortmunder export, a doppelbock, a dunkel, a dunkelweizen, an eisbock, a flanders red ale, a golden ale, a gose, a gueuze, a hefeweizen, a helles, an india pale ale, a kölsch, a lambic, a light ale, a maibock, a malt liquor, a mild, a märzenbier, an old ale, an oud bruin, a pale ale, a pilsner, a porter, a red ale, a roggenbier, a saison, a scotch ale, a stout, a schwarzbier, a vienna lager, a witbier, a weissbier, or a weizenbock.

In some embodiments, the ingestible beverage includes a foam collar retention that is about the same as, or improved with respect to, that of the beverage.

In some embodiments, the ingestible beverage includes a lace that is about the same as, or improved with respect to, that of the beverage.

In some embodiments, the ingestible beverage includes a specific gravity that is about the same as that of the beverage.

In some embodiments, the ingestible beverage includes a turbidity that is about the same as that of the beverage.

In some embodiments, the ingestible beverage includes

EXAMPLES

Example 1: Improved Focus

A beverage and a composition provided herein including one or more terpenes are mixed, and a subject ingests the mixed beverage. The subject experiences improved focus after consuming the mixed beverage.

Example 2: Improved Sedation

A beverage and a composition provided herein including one or more terpenes are mixed, and a subject ingests the mixed beverage. The subject experiences improved sedation after consuming the mixed beverage.

Example 3: Improved Energy

A beverage and a composition provided herein including one or more terpenes are mixed, and a subject ingests the mixed beverage. The subject experiences improved energy after consuming the mixed beverage.

Example 4: Improved Awareness

A beverage and a composition provided herein including one or more terpenes are mixed, and a subject ingests the mixed beverage. The subject experiences improved awareness after consuming the mixed beverage.

Example 5: Improved Head (i.e. Foam Collar) Retention

A beverage and a composition provided herein including one or more terpenes are mixed, and the mixed beverage is poured into a container. The mixed beverage exhibits an improved foam collar retention as compared to that of the beverage prior to mixing.

Example 6: Blind Taste Test Observational Survey

A taste testing study was performed in a social co-working space to determine consumer response to the following: experience of dosing beers with terpenes—enjoyment, shared and individually; resulting aroma change—likeability; resulting flavor change—acceptability, likability; resulting change in hop profile—opinion; resulting change in finish—smoothness; and resulting change over time—observations. Participants included 20 healthy volunteers (12 males and 8 females).

The observational survey was conducted as follows. A single-blind cross over design study was performed. On testing day, participants received a combination of two commercially available beer beverages from large globally distributed brands. Each corresponded to a sampled prototype. One light beer and a second medium lager beer.

To examine the first aim of the current study, i.e. the changes in aroma and taste after incorporating the terpene blend, each participant was asked to first smell, taste, and comment on their target beer before adding (which may be referred to herein as dosing) a sample beverage additive (i.e., a terpene blend). Then add a terpene composition from a vial and repeat the smell, taste, and comment process noting their observations on a prepared survey form by scoring their impressions.

Each beer was independently paired with two different samples that include the components shown in Table 2.

TABLE 2

Sample compositions.

| Sample # | Composition (% by weight/volume) |
|---|---|
| Sample 1 | β-Caryophyllene 20% |
| | Myrcene 18% |
| | α-Humulene 15% |
| | Terpinolene 15% |
| | α-Pinene 8% |
| | Linalool 5% |
| | Limonene 5% |
| | Farnescene 5% |
| | Geraniol 3% |
| | β-Pinene 2.5% |
| | delta 3-Carene 1.5% |
| | Citronellol 0.5% |
| | α-Terpineol 0.5% |
| | Camphene 0.2% |
| | p-Cymene 0.2% |
| | Nerolidol 0.2% |
| | Citrus flavoring >0%, ≤0.4% |
| Sample 2 | Myrcene 30% |
| | α-Humulene 30% |
| | β-Caryophyllene 19.4% |
| | Linalool 5% |
| | Farnescene 5% |
| | Geraniol 3% |
| | Limonene 2% |
| | α-Pinene 2.0% |
| | β-Pinene 2.0% |
| | Citronellol 0.5% |
| | α-Terpineol 0.5% |
| | Camphene 0.2% |
| | p-Cymene 0.2% |
| | Nerolidol 0.2% |
| Sample 3 | Sample 2 + Citrus flavoring |

Sample 1 is an uplifting blend featuring terpenes that add to focus and alertness and is intended to improve and enhance social interaction and personal control during an alcohol drinking experience. This blend was further designed to feature a pleasing aromatic appeal and overcome bitterness or flat flavors. The additional natural flavorings that create this added appeal are in a mix of a variety of citrus flavoring.

Sample 2 is also an uplifting blends featuring terpenes that add to focus and alertness and is intended to improve and enhance social interaction and personal control during an alcohol drinking experience. This composition is further designed to add to the aroma and taste of lager beers to enhance them with a hoppiness similar to that of IPA beers. This features a hops theme mix of terpene ingredients.

The terpene blend samples were prepared in a water-soluble format and filled in 1.5 mL vials. Each container was not labeled for participants to review prior to consumption, effectively blinding them from contents, thus preventing bias in an expected response. Each vial was identical in shape and weight, and participants had no knowledge of differences in the samples prior to adding, i.e. dosing, to the target beverages.

Flavor Assessment: the test required each 1.5 mL vial sample to be poured into a 12 oz cup containing the base beer. Each base beer was dosed with at least one prototype sample. More samples were added based on the profile of the base beer. Great attention was added to each respondent to first taste the base beer, record subjective responses on a scale of 1-10 based on their personal preference. After dose enhancing the base beer with prototype blends, the respondents would record subjective responses on a 1-10 scale, and only after adding the vial contents to the base beer and fully consuming the dosed beverage. Participants were able to control the pace and social interaction that would customarily coincide with consuming beer.

Aroma assessment: a questionnaire was used to evaluate the level of subjective aromatic preferences. Scores for each base beer plus added sample represented the degree of preferences and change in aroma ranging from 1 to 10 (10 being highest preference).

Consumer preferences and video verbatim commentary: additional questions were offered from the survey, including general alcoholic drinking preferences, beverage drinking preferences, age, income, ranking of beer and alcohol, and interest in purchasing infused or dose enhanced versions of the study prototype terpene blend.

Secondary video surveys were conducted which revealed verbatim testimony on the generalized effects, improvements in social interaction and general well-being from consuming the beers prior to and after adding the prototype terpene blend.

Data collection, statistics, and analysis: To show the effects on aroma, taste, well-being, awareness, and social interaction, a change score was calculated for each of the variables at each sample run by subtracting the pre-sample score from the post-sample score. Results are shown in Table 3 and Table 4.

In addition to collecting written responses via surveys verbatim comments from taste test participants were recorded. The participants were neither screened nor coached in any way. On aroma of the beer plus terpene blend composition, participant comments included: "it took a drink that I had no interest in and it made me want to experience it"; "[o]h, wow"; and "[t]his now smells sweet and citrusy; it smells nice; it makes me want to drink it." On taste and effect of the beer plus terpene blend composition, participant comments included: "it made the lager tastier"; "it made it a lot of fun"; "the longer it sat, the better it got"; and " . . . I'm alert, dude!"

TABLE 3

| STELLA | SCORES | | | | | | | | | |
|---|---|---|---|---|---|---|---|---|---|---|
| FIRST IMPRESSION | 1 | 2 | 3 | 4 | 5 | 6 | 7 | 8 | 9 | 10 |
| Baseline | 0% | 0% | 13% | 0% | 13% | 13% | 38% | 25% | 0% | 0% |
| Sample 2 + beer | 0% | 0% | 14% | 0% | 14% | 43% | 14% | 14% | 0% | 0% |
| Sample 3 + beer | 0% | 17% | 0% | 17% | 0% | 17% | 0% | 50% | 0% | 0% |
| Sample 1 + beer | 20% | 0% | 0% | 0% | 0% | 20% | 20% | 20% | 20% | 0% |
| AROMA | 1 | 2 | 3 | 4 | 5 | 6 | 7 | 8 | 9 | 10 |
| Baseline | 0% | 0% | 13% | 13% | 25% | 25% | 13% | 13% | 0% | 0% |
| Sample 2 + beer | 0% | 0% | 0% | 14% | 14% | 14% | 43% | 14% | 0% | 0% |
| Sample 3 + beer | 0% | 17% | 0% | 17% | 0% | 17% | 20% | 20% | 10% | 0% |
| Sample 1 + beer | 0% | 0% | 0% | 0% | 0% | 17% | 20% | 20% | 17% | 10% |
| TASTE | 1 | 2 | 3 | 4 | 5 | 6 | 7 | 8 | 9 | 10 |
| Baseline | 0% | 0% | 13% | 13% | 13% | 13% | 38% | 13% | 0% | 0% |
| Sample 2 + beer | 0% | 14% | 14% | 14% | 0% | 43% | 14% | 0% | 0% | 0% |
| Sample 3 + beer | 0% | 0% | 0% | 17% | 0% | 17% | 17% | 17% | 17% | 17% |
| Sample 1 + beer | 0% | 0% | 0% | 10% | 10% | 17% | 20% | 17% | 17% | 10% |
| HOPPINESS | 1 | 2 | 3 | 4 | 5 | 6 | 7 | 8 | 9 | 10 |
| Baseline | 25% | 0% | 0% | 38% | 25% | 0% | 13% | 0% | 0% | 0% |
| Sample 2 + beer | 0% | 0% | 14% | 14% | 14% | 14% | 0% | 43% | 0% | 0% |
| Sample 3 + beer | 0% | 17% | 0% | 17% | 0% | 0% | 0% | 33% | 17% | 17% |
| Sample 1 + beer | 20% | 10% | 10% | 20% | 0% | 0% | 20% | 20% | 0% | 0% |
| FINISH | 1 | 2 | 3 | 4 | 5 | 6 | 7 | 8 | 9 | 10 |
| Baseline | 14% | 0% | 0% | 0% | 29% | 0% | 57% | 0% | 0% | 0% |
| Sample 2 + beer | 0% | 0% | 0% | 0% | 0% | 33% | 17% | 33% | 17% | 0% |
| Sample 3 + beer | 17% | 17% | 17% | 0% | 0% | 0% | 33% | 17% | 0% | 0% |
| Sample 1 + beer | 0% | 0% | 0% | 0% | 20% | 20% | 20% | 20% | 10% | 10% |

TABLE 4

| MICHELOB ULTRA | SCORES | | | | | | | | | |
|---|---|---|---|---|---|---|---|---|---|---|
| FIRST IMPRESSION | 1 | 2 | 3 | 4 | 5 | 6 | 7 | 8 | 9 | 10 |
| Baseline | 10% | 30% | 20% | 20% | 20% | 0% | 0% | 0% | 0% | 0% |
| Sample 3 + beer | 0% | 0% | 0% | 13% | 13% | 38% | 25% | 13% | 0% | 0% |
| Sample 1 + beer | 0% | 0% | 0% | 0% | 20% | 40% | 0% | 10% | 10% | 20% |
| AROMA | 1 | 2 | 3 | 4 | 5 | 6 | 7 | 8 | 9 | 10 |
| Baseline | 30% | 50% | 10% | 0% | 0% | 10% | 0% | 0% | 0% | 0% |
| Sample 3 + beer | 0% | 0% | 13% | 0% | 25% | 25% | 13% | 25% | 0% | 0% |
| Sample 1 + beer | 0% | 0% | 0% | 0% | 10% | 10% | 20% | 30% | 10% | 20% |
| TASTE | 1 | 2 | 3 | 4 | 5 | 6 | 7 | 8 | 9 | 10 |
| Baseline | 0% | 30% | 30% | 10% | 10% | 20% | 0% | 0% | 0% | 0% |
| Sample 3 + beer | 0% | 0% | 0% | 13% | 0% | 38% | 25% | 25% | 0% | 0% |
| Sample 1 + beer | 0% | 0% | 0% | 0% | 20% | 10% | 20% | 20% | 20% | 10% |
| HOPPINESS | 1 | 2 | 3 | 4 | 5 | 6 | 7 | 8 | 9 | 10 |
| Baseline | 38% | 63% | 0% | 0% | 0% | 0% | 0% | 0% | 0% | 0% |
| Sample 3 + beer | 17% | 17% | 33% | 33% | 0% | 0% | 0% | 0% | 0% | 0% |
| Sample 1 + beer | 29% | 29% | 0% | 14% | 0% | 0% | 29% | 0% | 0% | 0% |
| FINISH | 1 | 2 | 3 | 4 | 5 | 6 | 7 | 8 | 9 | 10 |
| Baseline | 33% | 22% | 22% | 0% | 11% | 11% | 0% | 0% | 0% | 0% |
| Sample 3 + beer | 0% | 0% | 43% | 0% | 29% | 14% | 14% | 0% | 0% | 0% |
| Sample 1 + beer | 0% | 11% | 11% | 11% | 22% | 0% | 11% | 11% | 11% | 11% |

The terpene blends as a beer beverage enhancer show clear increases in scores for each tested Terpene Blend Enhancer sample. The observational evidence shows that the compositions provided herein have a profound and positive effect on alcoholic beverages such as widely available beers.

This was demonstrated with more ranked entries by participants for scoring between level 5 to 10 compared to both of the base beers where most scores were between 1 and 6 for each category of analysis, first impression, aroma, taste, and finish and was consistent for each terpene blend enhancer additive.

Surprisingly, data-points for finish (which refers to the taste/feeling after a real drink of the beverage) was assessed in both base beers (Michelob Ultra and Stella) which are well-known and commercially successful products. Overall, the finish scores demonstrated that 75% of participants thought both the base beers had a sub-par finish. These tasting data feedback also showed that sample 3 delivered a 100% lift in positive response. At the same time, sample 1 lifted the positive finish by over 100% and scored higher from previously ranked levels.

Additionally, the subjects recorded higher ranking scores for taste, aroma and hoppiness by the enhancement of sample 2 compared to a medium bodied base lager beer (Stella), thus elevating the experience beyond expectations.

This data set, along with the subjective comments of test participants, confirmed that the compositions provided herein are a unique blend of components that improves the drinking experience and sensations for the target beverages with consumers.

Example 7: Shelf Life Test

A shelf life test was run to determine the shelf life of a light lager beer infused with a beer beverage modifying terpene blend composition as described herein. The number of days or months a beverage can retain its new infused aroma, taste, or effect, following addition of a composition provided herein, at 3 months, 6 months, 9 months and 1 year was assessed. Previous commercial attempts at preserved or extended shelf life in beer have been conducted by large beer manufacturers, and were not known to result in any appreciable preserved organoleptic indicators (appearance, color, taste, or smell).

The compositions provided herein enhance the aroma, taste, and flavor of, for example, a light lager beer according to very positive taste tester reviews. Initially all reviews were conducted right after a flavor enhancer composition, as provided herein, was added to the freshly opened can or bottle of target beverage.

The test composition (Sample 2 of Table 2) was prepared in an emulsion. One case (12 Bottles) of Platinum Bud Light beer were opened and infused with a 1.5 mL dose of the test terpene blend composition and re-sealed. A second case of bottles, the control, was opened and re-sealed without adding anything into the bottles. Half the bottles in each group was stored at room temperature (20° C.) while the other half was stored in a refrigerator (4° C.). Bottles of infused beers and control bottles were tested by a group of 3-4 experienced beer drinkers after 3, 6, 9, 12, and 15 months of storage. To minimize photosensitivity of terpenes in the test composition, amber colored glass bottles were used.

Beer in both infused and control bottles after opening were well carbonated and foamy, which indicated that they were effectively and safely re-sealed.

Aroma, taste, and flavor of the infused beers remained stable, very distinct, and pleasant at time interval tested from 3 months to 15 months of storage both at the room temperature and when refrigerated. All reviewers noticed the difference and preferred the taste and flavor of infused beer over the control one.

Visual appearance, transparency, and foam collar retention was not apparent. The color of infused beer was a little darker after addition of the test composition. Infused beer remained otherwise clear and did not show any signs of oil separation neither on the top nor on the bottom.

What is claimed is:

1. A composition, comprising a first mixture including beta caryophyllene, myrcene, limonene, alpha humulene, linalool, alpha terpineol, and xanthohumol, wherein:

beta caryophyllene is present in the first mixture in a concentration of about 20% to about 40% v/v;

myrcene is present in the first mixture in a concentration of about 5% to about 40% v/v;

limonene is present in the first mixture in a concentration of about 2% to about 15% v/v;

alpha humulene is present in the first mixture in a concentration of less than 1% to about 15% v/v;

linalool is present in the first mixture in a concentration of less than 1% to about 5% v/v;

alpha terpineol is present in the first mixture in a concentration of less than 1% to about 5% v/v;

xanthohumol is present in the first mixture in a concentration of not more than about 20% v/v;

wherein the first mixture optionally includes one or more of beta pinene, alpha pinene, alpha bisabolol, valencene, terpinolene, trans ocimene, or delta 3 carene; and wherein the first mixture is present in the composition in a concentration of about 10 to 15 mg/mL.

2. The composition of claim 1, wherein the first mixture is present in the composition in a concentration of about 13.3 mg/mL.

3. The composition of claim 1, wherein the first mixture includes one or more of beta pinene, alpha pinene, alpha bisabolol, valencene, terpinolene, trans ocimene, or delta 3 carene and wherein:

beta pinene, when present in the first mixture, is present in the first mixture in a concentration of about 2% to about 10% v/v;

alpha pinene, when present in the first mixture, is present in the first mixture in a concentration of about 2% to about 10% v/v;

alpha bisabolol, when present in the first mixture, is present in the first mixture in a concentration of less than 1% to about 5% v/v;

valencene, when present in the first mixture, is present in the first mixture in a concentration of about 5% v/v or less;

terpinolene, when present in the first mixture, is present in the first mixture in a concentration of less than 1% to about 20% v/v;

trans ocimene, when present in the first mixture, is present in the first mixture in a concentration of less than 1% to about 5% v/v; and delta 3 carene, when present in the first mixture, is present in the first mixture in a concentration of less than 1% to about 5% v/v.

4. The composition of claim 1, further comprising one or more of L-theanine, caffeine, quercetin, green tea extract, vitamin $B_{12}$, or vitamin D.

5. The composition of claim 1, further comprising one or more of curcumin, cocoa, dark chocolate, galangal, ashwagandha, an adaptogen, or maca root.

6. The composition of claim 1, wherein the first mixture is encapsulated within a vesicle.

7. The composition of claim 1, further comprising one or more of vitamin A, vitamin $B_6$, vitamin C, vitamin D, vitamin E, vitamin K, thiamin, riboflavin, niacin, pantothenic acid, pyridoxal, cobalamin, biotin, folate, folic acid, calcium, phosphorus, potassium, sodium, chloride, magnesium, iron, zinc, iodine, sulfur, cobalt, copper, fluoride, manganese, or selenium.

8. The composition of claim 1, further comprising vitamin C, vitamin E, selenium, beta-carotene, lycopene, lutein, zeaxanthin, an anthocyanidin, a catechin, a coumarin, a flavan-3-ol, a flavanone, a flavanonol, a flavone, a flavonol, an isoflavone, a xanthone, or a combination thereof.

9. The composition of claim 1, further comprising:

1) *Lactobacillus helveticus, Bifidobacterium longum, Lactobacillus casei, Lactobacillus plantarum, Lactobacillus acidophilus, Lactobacillus delbrueckii* subsp. *bulgaricus, Bifidobacterium breve, Bifidobacterium infantis, Streptococcus salivarius, Lactobacillus rhamnosus, Lactobacillus gasseri*, or a combination thereof; or 2) an abyssinone, apigenin, biochanin, daidzein, diosmetin, epicatechin, eriodictyol, fisetin, genistein, hesperidin, kaempferol, luteolin, macluraxanthone, myricetin, naringenin, peonidin, quercetin, rutin, scopoletin, taxifolin, theaflavin, tricin, or a combination thereof; or 3) both 1) and 2).

10. The composition of claim 1, wherein the composition further includes 1) selenium and a flavonoid, 2) selenium and an antioxidant, or 3) selenium, a flavonoid, and an antioxidant.

11. A nutritive ingestible food or beverage or food or beverage additive, comprising the composition of claim 1.

12. A non-nutritive ingestible food or beverage or food or beverage additive, comprising the composition of claim 1.

13. An emulsion, comprising particles, said particles including the composition of claim 1 encapsulated within a vesicle.

14. The emulsion of claim 13, wherein the vesicle is a lipid bilayer vesicle.

15. An emulsion, comprising:

1) about 2 wt % cannabidiol (CBD) oil or the composition of claim 1, about 2 wt % polysorbate 80, about 1 wt % lecithin, and about 95 wt % water; or 2) about 5 wt % CBD oil or the composition of claim 1, about 3.3 wt % polysorbate 80, about 1.7 wt % lecithin, and about 90 wt % water.

16. A kit, comprising the composition of claim 1, and instructions for use thereof.

17. A method, comprising ingesting the composition of claim 1.

18. The composition of claim 1, wherein the composition is encapsulated within a vesicle having a droplet diameter of about 170 nM to about 300 nM.

19. A composition, comprising:

a first mixture including beta caryophyllene, myrcene, limonene, alpha humulene, linalool, alpha terpineol and xanthohumol; and wherein the composition is encapsulated within a vesicle having a droplet diameter of about 170 nm to about 300 nm.

* * * * *